US006444210B1

(12) United States Patent
Kournikakis et al.

(10) Patent No.: US 6,444,210 B1
(45) Date of Patent: Sep. 3, 2002

(54) BACTERIAL AND SYNTHETIC POLYSACCHARIDE IMMUNOMODULATORS THAT ENHANCE GENERAL IMMUNITY

(75) Inventors: Bill Kournikakis; Maureen L. Simpson; John W. Cherwonogrodzky, all of Medicine Hat (CA)

(73) Assignee: Her Majesty the Queen in right of Canada, as represented by the Minister of National Defence of Her Majesty's Canadian Goverment, Ottawa (CA)

( * ) Notice: Subject to any disclaimer, the term of this patent is extended or adjusted under 35 U.S.C. 154(b) by 0 days.

(21) Appl. No.: 08/882,398

(22) Filed: Jun. 25, 1997

Related U.S. Application Data

(60) Provisional application No. 60/021,112, filed on Jul. 3, 1996.

(51) Int. Cl.[7] ........................ A61K 39/02; A61K 39/29; A61K 39/106; A61K 45/00

(52) U.S. Cl. ................................ 424/252.1; 424/189.1; 424/261.1; 424/278.1; 424/279.1

(58) Field of Search ........................... 424/184.1, 252.1, 424/261.1, 278.1, 279.1

(56) References Cited

U.S. PATENT DOCUMENTS

| | | | | |
|---|---|---|---|---|
| 4,734,402 A | * | 3/1988 | D'Hinterland et al. | 514/54 |
| 4,734,403 A | | 3/1988 | D'Hinterland et al. | 514/54 |
| 4,900,722 A | * | 2/1990 | Williams et al. | 514/54 |
| 4,933,440 A | | 6/1990 | D'Hinterland et al. | 536/53 |
| 4,937,327 A | * | 6/1990 | D'Hinterland et al. | 536/1.1 |
| 5,006,463 A | * | 4/1991 | Cherwonogrodzaky | 435/7.32 |

FOREIGN PATENT DOCUMENTS

| | | |
|---|---|---|
| CA | 2164155 | 11/1995 |

OTHER PUBLICATIONS

Bundle et al FEBS Lett. 216: 261–4 1987.*
Bundle et al Infection & Immunity 46:384–388, 1984.*
Cherwonogrodzky et al Arch. Med. Vet. XXVII No Extraordinario 29–37, 1995.*
Wong et al Immunology 77:123–128, 1992.*
Jacques et al Vaccine 9:896–900, 1991 (1).*
Cherwonogradzky et al The Internation Congress for Infections Diseases, Abstract 11029, Jun. 10–13, 1996.*
Jacques et al Vaccine 9:559–563, 1991 (2).*
Cherwonogrodzdzky et al Polysaccharides of Brucellis, Animal Brucellosis, Nielsen, J R. Duncan Ed. pp. 19–64, (1990).*
Elzer et al "Antibody–mediated protection against *Brucella abortus* in BALB/c mice at successive periods after infection: variation between virulent strain 2308 and attenuated vaccine strain 19", Immunology, vol. 82, pp. 651–658, Jun. 1, 1994.*
Bundle et al., "The Structure of the Lipopolysaccharide O–chain . . . ", FEBS Letters, vol. 216, No. 2, Jun., 1987, pp. 261–264.
Caroff et al., "Structure of the O–chain of the Phenol–Phase Soluble . . . ", Eur. J. Biochem., 139, FEBS 1984, pp. 195–200.
Caroff et al., "Antigenic S–Type Lipopolysaccharide . . . ", Infection and Immunity, vol. 46, No. 2, Nov., 1984, pp. 384–388.
Cherwonogrodzky et al., "Polysaccharides of Brucella", Animal Brucellosis, K. Nielsen, J. R. Duncan (ed.), 1990, pp. 19–64.
Cherwonogrodzky et al., "Effect of D–Tryptophan on Hemolysin . . . ", Journal of Clinical Microbiology, vol. 20, No. 5, Nov., 1984, pp. 909–911.
Cherwonogrodzky et al., "A Polysaccharide Vaccine to Enhance Immunity Against Brucellosis", Arch. Med. Vet. XXVII, N° Extraordinario, 1995, pp. 29–37.
Cherwonogrodzky et al., ". A Polysaccharide Vaccine to Enhance . . . ", 7$^{th}$ Int'l. Congress for Infectious Diseases, Hong Kong, Jun., 1996, Abstract No. 11029.
Kournikakis et al., "Optimization of a Phagocyte Microplate . . . ", J. Biolumin Chemilumin, 10, 1995, pp. 63–67.

* cited by examiner

*Primary Examiner*—Rodney P Swartz
(74) *Attorney, Agent, or Firm*—Nixon & Vanderhye P.C.

(57) ABSTRACT

The present invention relates to the effects of bacterial polysaccharides on cell mediated immunity in animals. Polysaccharides of the present invention comprise the outer polysaccharides (OPS) located on bacterial cell membranes and other polysaccharides (e.g. "Poly B") either secreted or contained within the periplasmic space. These polysaccharides have been found to enhance the general or cell mediated immunity of animals to various diseases. The invention provides for the use of such polysaccharides in preventing and treating various infections as well as in treating carcinomas. The invention also provides for synthetic polysaccharides having the same immuno-modulating effect as the bacterial polysaccharides.

26 Claims, 3 Drawing Sheets

Sets of 5 mice were used.
Concentration of *B. abortus* OPS was 5 mg/mouse.
Polysaccharide or phosphate buffered saline (PBS) control injected intra-peritoneally on day 0.
On day 7, mice were sacrificed and assayed for neutrophil/macrohpage activity.
Ratio of macrophage cells to opsonized zymosan particles was 1:40.
Each well had 5 X $10^5$ macrophages, 2 X $10^7$ zymosan particles.

Figure 2

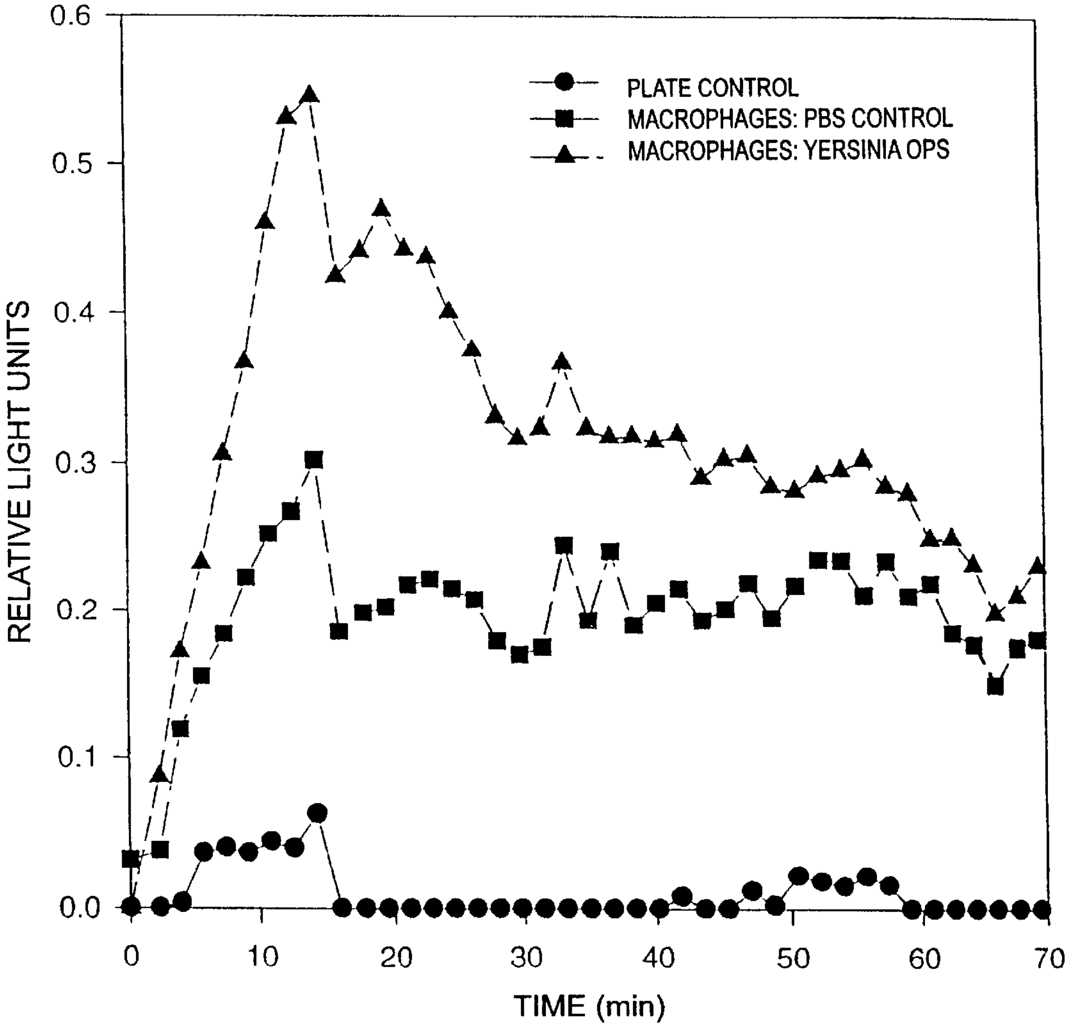

Sets of 5 mice were used.
Concentration of *Y. enterocolitica* 0:9 OPS was 5 mg/mouse.
Polysaccharide or phosphate buffered saline (PBS) control injected intra-peritoneally on day 0.
On day 7, mice were sacrificed and assayed for neutrophil/macrohpage activity.
Ratio of macrophage cells to opsonized zymosan particles was 1:80.
Each well had 2.5 X $10^5$ macrophages, 2 X $10^7$ zymosan particles.

Figure 3

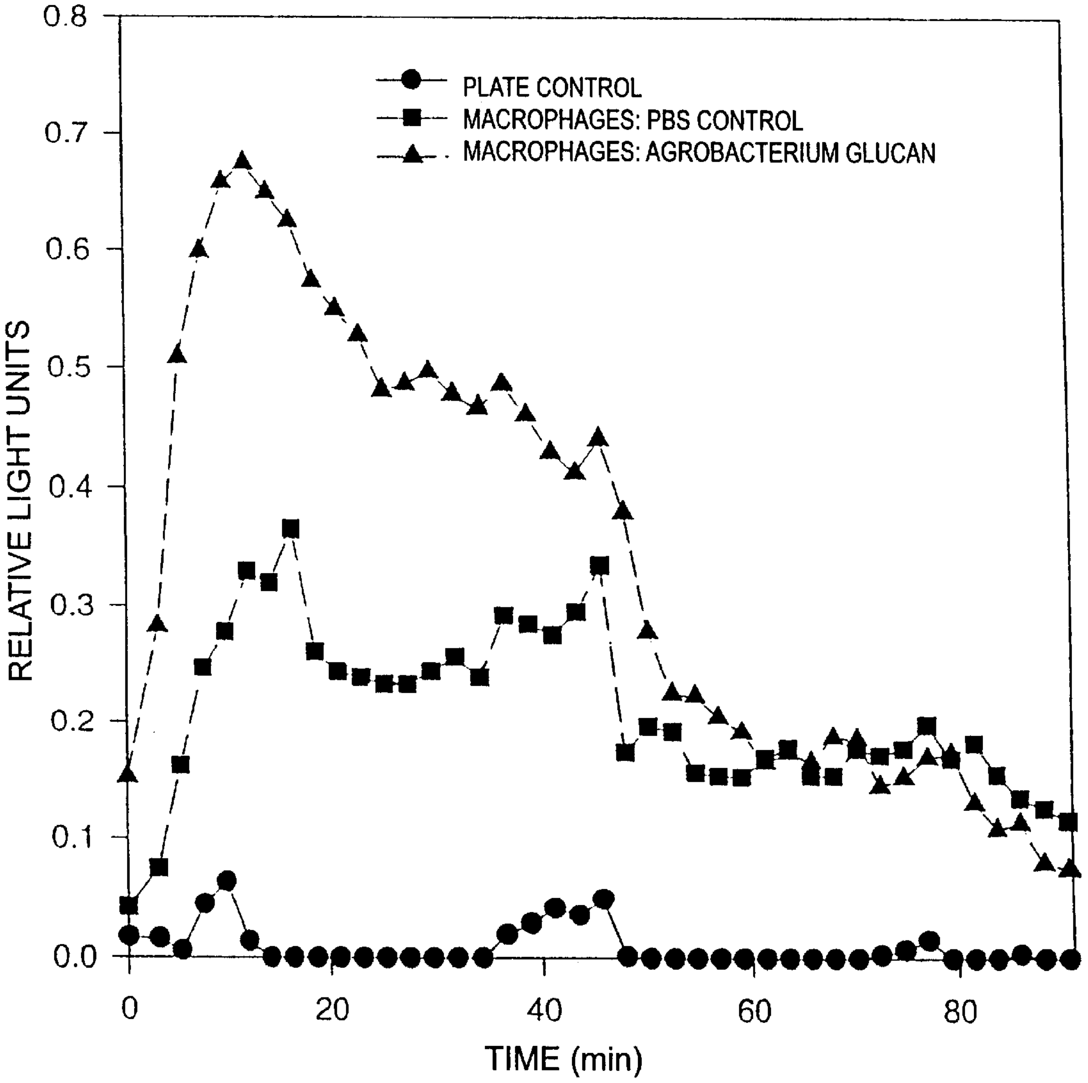

Sets of 5 mice were used.
Concentration of *Agrobacterium tumefaciens* 1,2-beta linked glucan was 5 mg/mouse.
Polysaccharide or phosphate buffered saline (PBS) control injected intra-peritoneally on day 0.
On day 7, mice were sacrificed and assayed for neutrophil/macrohpage activity.
Ratio of macrophage cells to opsonized zymosan particles was 1:40.
Each well had 5 X $10^5$ macrophages, 2 X $10^7$ zymosan particles.

BACTERIAL AND SYNTHETIC POLYSACCHARIDE IMMUNOMODULATORS THAT ENHANCE GENERAL IMMUNITY

The present application is based on, and claims benefit of, U.S. Provisional Application No. 60/021,112, filed, Jul. 3, 1996.

BACKGROUND OF THE INVENTION

Infectious agents, parasitic diseases or cellular pathologies are becoming more resistant to conventional methods of protection or treatment. These methods include vaccines, antibiotics, or immuno-modulating drugs. In controlling disease, one field that is gaining momentum is the development of compounds that stimulate the body's natural defences. These natural defences have been simplified as being of two responses: humoral immunity and cell mediated immunity.

Humoral, or specific, immunity involves the production of specific antibodies in an infected animal as a result of the presence of an invading microorganism or toxin having a particular antigen. These antibodies either congeal or inactivate the invader, or interact with other blood components, such as complement (a system of plasma proteins that interact with antibodies), to destroy it.

Cell mediated (cellular) immunity involves, in part, the activation of phagocytic cells in the host animal to become metabolically more active and digest or chemically neutralize invading foreign objects.

There are difficulties in stimulating either of these defences. In the case of humoral immunity: it requires several months of immunization to develop a response; antibody levels resulting from this form of immunity diminishes over several months; not all vaccines are effective in triggering an immune response (e.g. susceptibility to Dengue Fever actually increases with experimental vaccination); humoral immunity is useless against parasitic diseases (which invade the cells and are protected from antibodies or drugs); and, it is very specific to the serotype of a given microbe.

With cell meditated immunity, "immuno-modulators", or drugs that stimulate activity, enhance cellular activity either poorly or with little effect. Further, these compounds are frequently toxic (resulting in nausea, fevers, malaise and death), and may have unwelcome side effects on the activity of other cell sub-populations. Examples of such immuno-modulators are nucleic acid analogues, chemically defined drugs, adjuvants and biologically active peptides. These drugs are useful for only certain diseases.

One group of immuno-modulators that appears to have become overshadowed by other modulators are glycans which are carbohydrates extracted from micro-organisms, especially plants and yeast (Seljelid et al, 1981, "Glycan Stimulation of Macrophages in vitro", Exp. Cell. Res. 131:121–129). Glycans are also referred to as glucans, but in this report the term glucans will be used to refer to polymers of glucose. Seljelid et al (1981) found that "only insoluble glycans are effective in stimulating macrophages" and, of these glycans, the presence of 1,3-beta linkages of the sugars was believed to be a contributing factor.

D'Hinterland et al in U.S. Pat. No. 4,734,403 (issued Mar. 29, 1988) isolated a membrane polysaccharide from bacteria which was found to have an immuno-modulating effect on natural killer cells to destroy Maloney's lymphoma. The polysaccharide taught in this patent comprises a chain of galactofuranose and galactopyranose units and is isolated from gram negative bacteria. In U.S. Pat. Nos. 4,933,440 and 4,937,327, d'Hinterland et al teach immuno-modulators derived from the bacterial polysaccharides recited in the 4,734,403 patent.

The polysaccharide noted by d'Hinterland et al is extracted by cellular disruption, alkaline digestion and dissolving in water; it is unknown whether this polysaccharide can protect against its source bacterium, *Klebsiellapneumoniae*. As most immuno-modulators act only for a few days, this may be why the in vivo trials disclosed in the d'Hinderland references were conducted at most 3 days after immunization. The polysaccharide had adjuvant properties for enhancing antibodies (i.e. humoral immunity not cellular immunity) when it was given at the same time as a ribosomal vaccine. These publications are encouraging for other researchers, not only because of the anti-cancer properties of d'Hinderland's discovery, but also because of their findings that bacterial polysaccharides may have immunological effects.

In contrast, the present inventors have discovered that the O-polysaccharide (OPS) of Brucella used previously to either differentiate infected from vaccinated cattle (Cherwonogrodzky et al., U.S. Pat. No. 5,006,463) or to protect animals from brucellosis (Cherwonogrodzky et al., Canadian application 2,164,155), has immunomodulating properties. Although this polysaccharide is associated with the cell membrane when bound to lipopolysaccharide or LPS, in strain *B. melitensis* B 155 it is found loose in the periplasmic space, in *B. melitensis* 16M it is shed into the medium, and there is still controversy if it can form a capsule or form "native hapten" which is secreted away from the cell. Also, another polysaccharide associated with Brucella but not found in many other bacteria, referred to herein as "poly B", has similar immunomodulating effects in that it can also greatly increase the activity of macrophages as evidenced by chemilumenescence. These polysaccharides differ in composition, structure and sometimes location to the polysaccharide noted by d'Hinterland and these are purified by different methods. These polysaccharides (there is more known about the OPS) appear to have some different properties compared to the one presented by d'Hinterland.

SUMMARY OF THE INVENTION

Accordingly, in one embodiment, the present invention provides an immuno-modulating compound comprising an effective, non-toxic quantity of bacterial polysaccharide for enhancing cell mediated immunity in an animal against bacteria, fungi, yeast, viruses, parasites and cellular abnormalities.

The polysaccharides of the invention comprise bacterial OPS and Poly B molecules and polysaccharides cross reactive therewith and mixtures thereof.

Further, the invention provides for the use of such polysaccharides in the treatment and prevention of various infections as well as the treatment of carcinomas and other cellular pathologies.

BRIEF DESCRIPTION OF THE DRAWINGS

These and other features of the preferred embodiments of the invention will become more apparent in the following detailed description in which reference is made to the appended drawings wherein.

Figure 1:
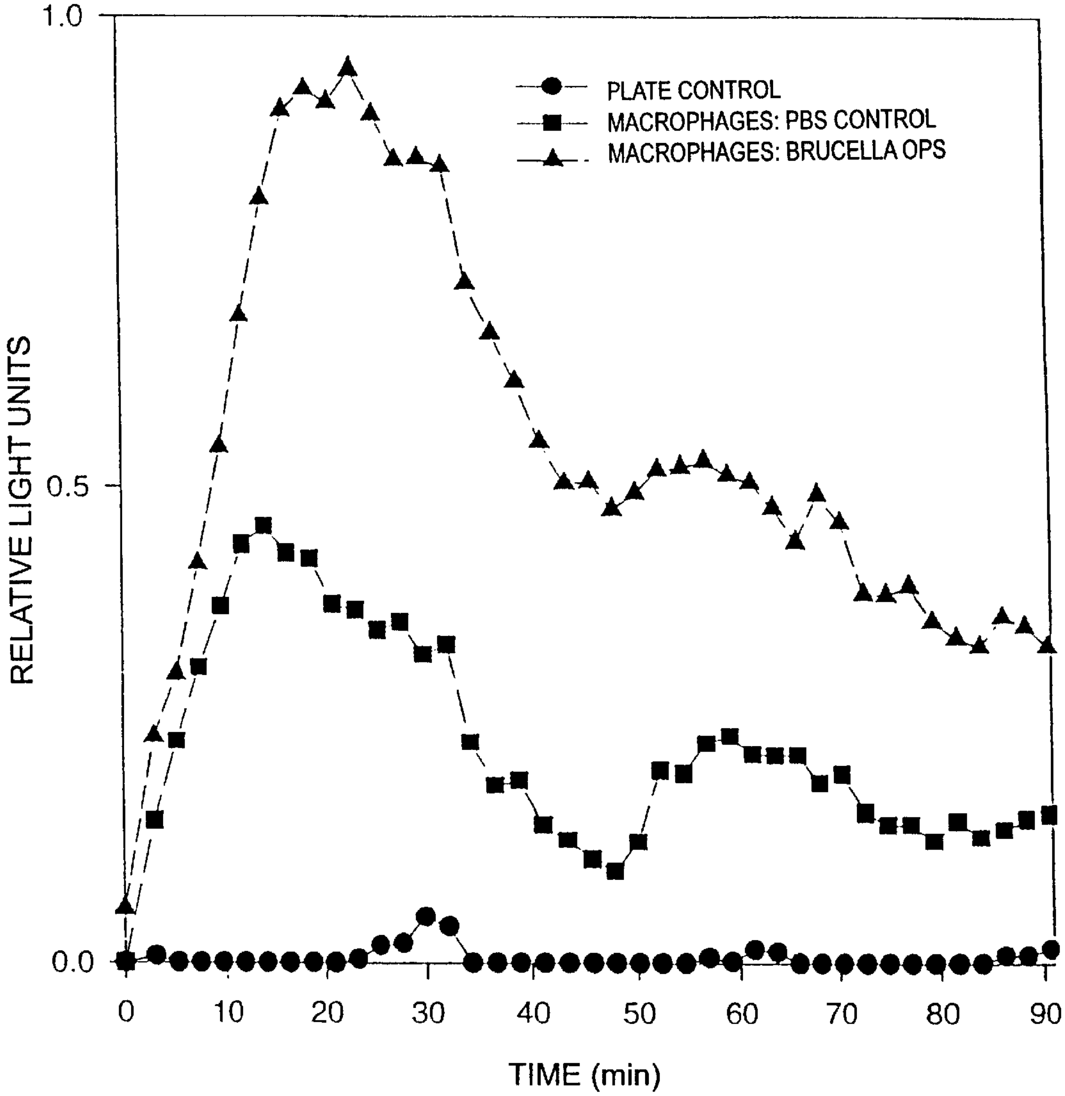
FIG. 1 is a graph showing the effect of *Brucella abortus* 0-polysaccharide (OPS) for enhancing neutrophil/ macrophage activity of Balb/c mice as determined by chemiluminescence assay.

FIG. 2 is a graph showing the effect of *Yersinia enterocolitica* 0-9 0-polysaccharide (OPS) for enhancing neutrophil/macrophage activity of Balb/c mice as determined by chemiluminescence assay.

FIG. 3 is a graph showing the effect of *Agrobacterium tumefaciens* 1,2-beta linked glucose polymer for enhancing neutrophil/macrophage activity of Balb/c mice as determined by chemiluminescence assay.

DETAILED DESCRIPTION OF THE PREFERRED EMBODIMENT

Although bacterial polysaccharides have been used as vaccines to enhance specific humoral immunity (i.e. to increase antibodies in the blood towards a specific antigen), the present invention uses such compounds to enhance general cellular immunity against a wide variety of microorganisms.

The inventors have found that soluble carbohydrate polymers, extracted from bacteria, can serve as potent immuno-modulators, stimulating the defences of white blood cells. In this investigation, the immuno-modulating effects of OPS (outer polysaccharide) from *B. abortus* was studied along with that from *Yersinia enterocolitica* O:9, a bacterium unrelated to the former but which synthesizes a similar OPS.

A study of the immunological effects of Brucella OPS found it to be an effective vaccine for preventing brucellosis in swine. A description of this study is found in Applicant's co-pending Canadian patent application number 2,164,155, filed Nov. 30, 1995. From the results of this study, it was also found that the OPS from Brucella also had immuno-modulating effects. The observations leading to this finding were as follows:

1. The antibody response was feeble to non-existent, as determined by measuring titres of IgG and IgM specific to OPS.
2. Where antibodies were induced either with the use of adjuvants liposomal encapsulation, high doses and/or multiple injections of this component, protection from infection was improved when the humoral immunity was reduced. An example of such adjuvants is Lipid A bound to OPS when smooth-lipopolysaccharide, or sLPS, is used.
3. The immunity that resulted from this vaccine seemed generic rather than specific. Not only did it protect animals from different species of Brucella (e.g. mice and guinea pigs from *B. abortus*, swine from *B. suis*), but it also protected swine from an outbreak of *Haemophilus pleuropneumoniae.*
4. The OPS was exceptionally potent and long lasting. 100 $\mu$g of the OPS protected a sow that was immunized at 2 months of age and 25 kg in weight. Such protection was evident when the sows were challenged 6 months later and continued one year later. During this time antibody titres were not detectable.

Further, an investigation was made of the immuno-modulating effects of a glucose polymer, referred to as "Polysaccharide B" or "Poly B," synthesized by *Brucella abortus.* Poly B is one of a number of unusual sugars (i.e of unusual conformation and/or linkages) produced by Brucella as well as several other bacteria (including plant pathogens such as *Agrobacterium tumefaciens*) and is a circular molecule comprising a ring of 1,2-linked-β-D-glucose. This compound, whose function is unknown, cannot be digested and has not been found to induce an antibody response; however, it has been found to be a powerful immuno-modulator. To avoid the possibility of the immuno-modulating activity being caused by contamination by Brucella OPS, the source of this cyclic glucan (glucose polymer) was *Agrobacterium tumefaciens.*

The Brucella OPS comprises a polymer of 4-formamido-4,6-dideoxy-D-mannose having a molecular weight of about 15,000 to 18,000. Specifically, this OPS is composed of a repeating pentasaccharide unit containing a sequence of one 1,3- and four 1,2-linked 4,6-dideoxy-4-formamido-α-D-mannopyranosyl units. The Poly B molecule has been identified as a family of circular 1,2- linked polymers of β-D-glucopyranosyl units ranging in ring size from 17 to 24 glucosyl units (Bundle et al, 1987, "The Structure of the Lipopolysaccharide O-Chain (M Antigen) and Polysaccharide B Produced by *Brucella melitensis* 16M", FEBS Lett., 216:, 261–264). Further, the Poly B used in the present study is not located on the cell membrane but in the periplasmic space.

Evidence from swine trials supports the view that these immuno-modulators can protect against a broad range of infections (e.g. different Brucella species, *Haemophilus pleuropneumoniae*). It is also expected that these immuno-modulators can also act as therapeutic agents following infection. Unlike the view expressed by Seljelid et al. (1981), the O-polysaccharides of either *B. abortus* or *Y enterocolitica* O:9 are polymers of 4-formamido-4,6-dideoxy-D-mannose with 1,2 alpha and 1,3 alpha (not beta) linkages (Caroff et al, 1984, "Structure of the O-Chain of the Phenol Phase Soluble Cellular Lipopolysaccharide of *Yersinia enterocolitica* Serotype O:9", Eur. J. Biochem., 139, 195–200; Caroff et al, 1984, "Antigenic S-Type Lipopolysaccharide of *Brucella abortus* 1119–3", Infect. Immun. 46, 384–388; Cherwonogrodzky, 1995, "A Polysaccharide Vaccine to Enhance Immunity Against Brucellosis", Arch. Med. Vet., 27, 29–37).

There is anecdotal evidence that these polysaccharides can enhance the immune response to vaccines against viral diseases, even when given before vaccination. When investigators were immunized against Western Equine Encephalitis (WEE), the average titre was 103±117. An investigator working on these noted polysaccharides (and who was likely to have been exposed to trace amounts of these polysaccharides prior to immunization), following WEE vaccination, had titres greater than 10,000.

Of the several thousands of bacterial OPS's available for study, the above findings make it logical to begin with the OPS of Brucella species that have shown positive results, then to progress to the OPS of bacteria that cross-react with Brucella (e.g. the OPS of *Y. enterocolitica* O:9), and then investigate other bacterial OPS, such as Poly B for immuno-modulating effects. OPS and Poly B may appear to be very different sugars, but these were tested because these both have unusual compositions or structures. By unusual it is meant that such compositions or structures are unlikely to be a part of normal mammalian metabolism. Indeed, by being unusual these sugars may not be metabolized normally and hence act as metabolic signals for cellular immunity. OPS is a formamido sugar with 1,2 and 1,3α linkages and Poly B is 1,2β linked glucose in a circle.

MATERIALS AND METHODS

Preparation of Bacterial Compounds

*Brucella abortus* strain 413 was acquired from Agriculture Canada, Animal Diseases Research Institute (ADRI- Nepean), Nepean, Ontario, Canada. Bacteria were grown in Brucella broth (Difco/BDH Inc., Edmonton, Alberta) and incubated with 5% $CO_2$ at 37° C. for a week. The cells were killed with 2% phenol. To extract OPS, the method of Cherwonogrodzky et al. ("Antigens of Brucella, *Animal Brucellosis*, K. Nielsen and J. R. Duncan(eds.), CRC Press, Boca Raton, 19–64, 1990) was used. Briefly, the killed cells were suspended in 2% acetic acid in 1% saline (the suspension was 20% cells, v/v), placed in a boiling water bath for 2 hours, centrifuged to remove cells, trichloroacetic acid (final concentration of 0.2 M) was added to remove proteins, this was centrifuged and the supernatant was extracted at room temperature with an equal volume of phenol. The OPS was precipitated from the phenol layer with 5 volumes of methanol with 1% sodium acetate (w/v), dialyzed against 0.4% acetic acid/0.4% pyridine as buffer, then purified on a G-50 Sephadex™ column with this same buffer. Eluted OPS was lyophilized and kept as a dry powder until required.

The OPS of *Yersinia enterocolitica* O:9 was purified by the method of Caroff et al. (1984) which is similar to that noted above.

*Agrobacterium tumefaciens* 15955 was acquired from the American Type Culture Collection (ATCC) (Rockville, MD). It was grown in 4 liters of 1.5% glucose, 0.2% calcium carbonate supplemented with about 0.5% yeast extract of less than 8000 m.w. (40 grams of yeast extract was suspended in about 200 ml of distilled water, dialyzed and the contents outside the dialysis bag was used for the media) for 4 days at room temperature with constant stirring. At the end of this incubation, the culture was killed with 2% phenol, cells were removed with centrifugation, and the glucans were precipitated from the supernatant with 4 volumes of methanol with 1% sodium acetate. The precipitate was collected by centrifugation and, after discarding the supernatant, dissolved and dialyzed against distilled water, then lyophilized and kept as a dry powder until required.

Swine Trials 0.1 to 0.5 mg of *B. abortus* or *B. suis* OPS was dissolved in 1 ml of sterile 0.85% saline and injected into the jugular veins of sows. Alternatively, 0.1 to 0.5 mg of OPS was packed into a hole drilled into a pecan nut and fed to the swine. Sets of 10 swine were given either single or multiple (3 doses) inoculations. Swine were immunized at 2 months of age when they were about 25 kg, and then, 6 months later, were mated with 4 boars that were infected and shedding *B. suis* in the semen. A year later the sows were mated with infected boars again to determine if the vaccine had long lasting protection.

Measuring Enhanced White Blood Cell Activity

To measure immuno-modulation, a microplate chemiluminescent assay was used, based on the method of Kournikakis and Simpson ("Optimization of a Phagocyte Microplate Chemiluminescent Assay", 1995, J Biolumin. Chemilumin., 10). In brief, Balb/c mice (15–16 grams, 29–35 day old females) were purchased from Charles River, St. Constant, Quebec. Sets of 5 mice were injected with bacterial compounds in phosphate buffered saline (PBS), or as a control only PBS was used, intraperitoneally in 1.0 ml. Seven days later, the mice were sacrificed by cervical dislocation. 5 ml of Hank's balanced salt solution without sodium bicarbonate (HBSS-) (Gibco laboratories, Grand Island, N.Y.) was injected into the abdomen with a syringe having a 22 gauge, 1 inch angiocatheter attached and this was inserted into the peritoneal cavity. The abdomen was then massaged for 3 minutes, and the macrophage suspension was drawn off into the syringe. This was repeated twice more and all suspensions for a set of mice were pooled and diluted to a cell concentration of 1.0×10 cells/ml in Hank's balanced salt solution with $CaCl_2$ (HBSS+). The pooled suspension was centrifuged at 250 g for 10 min. The resulting pellet was re-suspended in 7 ml HBSS- and layered over 3 ml Histopaque™ 1083 (Sigma Chemical Col., Mo.). This was centrifuged at 700 g for 35 minutes. The cell layer was then collected and washed two times in HBSS-.

Phagocytic activity of macrophages was judged by enhanced luminescence of cells as a result of ingesting Lucigenin™ (Sigma Chemical Co., St. Louis, Mo.) when the neutrophils/monocytes phagocytized zymosan particles. These particles were prepared by boiling Zymosan A™, Sigma Chemical Co., collecting the insoluble particles and opsonizing with antibodies by incubating with human serum; see Kournikakis and Simpson, 1995). 100 $\mu$L of lucigenin™ was added to each well of a Titertek™ fluoroplate. 50 $\mu$L of the white blood cell suspension was added and after an incubation of 37° C. for 10 min, the Luminoskan™ control program added 100 $\mu$L of zymosan particles automatically. Luminescence was detected and recorded automatically by the Titertek™ Luminoskan™ (ICN Biomedicals, Inc., Huntsville, Ala.).

Western Equine Encephalitis Vaccination

Seven researchers were immunized with the Western Equine Encephalitis vaccine (formaldehyde killed strain CM-4884, produced by the Salk Institute, Swiftwater, Pa. USA). Administration was 3 subcutaneous doses, each given months apart. The vaccinated researchers were noted as belonging to either of 2 groups: six had good titres to the vaccine and had not worked with the polysaccharides noted in this invention, one had extraordinarily high titres and did work with these polysaccharides.

Results

1. Animal Studies

The use of *B. abortus* OPS to protect mice from brucellosis has been reported (Cherwonogrodzky et al, 1995) as has its use to protect guinea pigs and swine (Cherwonogrodzky et al., 1996, "A Polysaccharide Vaccine to Enhance Immunity Against Brucellla Species, $7^{th}$ Intl. Conf. for Infec. Dis., Hong Kong, abstract 11029). For the latter, swine given 0.1 mg to 0.5 mg, whether as a single dose or three doses each 1 week apart, or given intravenously or orally, were protected from brucellosis 6 months after immunization. One year later, the swine were still protected from brucellosis. Two months later, vaccinated swine were protected from an outbreak of *Haemophilus pleuropneumoniae* which either made ill or killed unvaccinated control swine.

2. Immuno-Modulation of Mice

Immuno-modulation of mouse macrophages was shown indirectly by the ingestion of the luminescent agent, lucigenin™, when these cells phagocytized zymogen particles. FIG. 1 shows that even though untreated mice had macrophages that were viable and active against this foreign agent, mice treated with *B. abortus* OPS (5 mg/mouse) had twice the phagocytic activity of controls. FIG. 2 also shows that this doubling of activity could be caused by OPS from *Y. enterocolitica* O:9, a bacterium that is unrelated but cross-reacts with Brucella. As noted above, it is suspected that bacterial carbohydrate polymers of unusual conformation or linkage might cause similar immuno-modulation. When the glucose polymer secreted by *Agrobacterium tume-*

*faciens* was tested, a dose of 5 mg per mouse caused similar effects, namely a doubling of macrophage phagocytic activity to foreign zymosan particles.

3. Immnuno-Modulation of Humans

Immuno-modulation of humans was shown indirectly by the observation that an investigator working with these polysaccharides (likely to have been exposed to trace amounts of these in the past) had exceptionally high titres to Western Equine Encephalitis vaccine. The investigator had not been working with the polysaccharides for a year prior to vaccination. The table below shows an obvious high response to this vaccine. The average titre (not counting investigator #1) was 103±117. Investigator #1 had at least 100-fold more than this.

TABLE 1

Results of Western Equine Encephalitis Vaccination

| Investigator | Serum WEE titers |
|---|---|
| #1 | Off the scale, greater than 10,000 (worked several times over several years with OPS, likely to have been exposed to OPS or Poly B) |
| #2 | 320 |
| #3 | 160 |
| #4 | 160 |
| #5 | Less than 10 |
| #6 | Less than 10 |
| #7 | 20 |

DISCUSSION

Although the noted sugar is uncommon among the bacterial OPS studied so far, it does appear to be common in the OPS of a small group of bacteria that are both invasive and pathogenic. The reason for this correlation (put forward by Cherwonogrodzky et al, 1990) is unknown, but there are two possibilities. The first is that the noted sugar has unusual properties. Although it easily dissolves in water, it is also very hydrophobic and will sequester into the phenol layer of a phenol-water extraction. This hydrophobic nature may allow it to insert itself into mammalian membranes, initiating the invasive process, or interfere with the cell's metabolism in much the same way that hormones attach to membrane receptors and regulate internal activity. The second possibility is that it may interact with the host's internal cellular enzymes, giving the bacterium an advantage for surviving in a normally hostile environment. As one example, some bacteria and yeasts do not metabolize unusual amino acid analogues. However, D-tryptophan will both inhibit growth and greatly enhance toxin expression in *Vibrio parahaemolyticus*. Possibly if an unusual carbohydrate does not overwhelm the eucaryotic cell, the cell responds to a metabolic abnormality by initiating cellular immunity as an automatic defence.

Although the mechanism for this immuno-modulation is being elucidated, the effect of bacterial polysaccharides to enhance cellular immunity is evident. FIGS. 1 to 3 show a doubling of phagocytic activity in response to a foreign particle. It should be noted that zymosan is an extract from yeast and hence an increase in phagocytic activity against this compound is likely to indicate an activity against yeast in general. Even before these experiments were done, it was clear that bacterial polysaccharides had an unusual effect on the macrophages as these congregated at the site of bacterial polysaccharide injection when the animals were sacrificed 1 week later. Practical applications were also discovered accidentally when swine immunized almost 2 years previously with *B. abortus* OPS resisted an outbreak of *Haemophilus pleuropneumoniae* that made ill or killed unvaccinated swine.

Although the chemiluminescent assays with mice have given evidence that supports the belief that bacterial polysaccharides can act as immuno-modulators, the accidental outcome in the above noted swine study, and the bizarre observation with human vaccination, is far more encouraging. In the mouse study, high doses of polysaccharides (5 mg of polysaccharide per 25 gram mouse) were necessary for enhancing white blood cell activity that was only tested 1 week later. In the swine study, low doses of polysaccharide (0.1 mg of polysaccharide per 25 kg sow was tested, and lower doses might be equally effective) enhanced their immunity which was challenged almost 2 years after treatment. It should be noted that in the scientific community it is believed that swine are closer animal models to humans than are mice. The foregoing study has found that bacterial polysaccharides enhance general cellular immunity and protect swine from 2 dissimilar bacteria, *B. suis* and *H. pleuropneumoniae*. Therefore, a further logical embodiment of the present invention is that components from one source can be used either before (to protect) or after (as treatment) infections caused by other bacteria, fungi, yeasts, parasites or viruses (e.g. HIV). It should be noted that in regards to immunity to viruses, an investigator who has prepared and researched the noted polysaccharides had (as shown in Table 1 above) at least 100-fold more anti-WEE antibodies than expected, even though the investigator had not worked with the polysaccharides for at least a year prior to vaccination. Cellular immunity is also important in clearing cellular abnormalities or pathologies, such as cancer (carcinomas) and the like, and a logical extension of this work is to use bacterial polysaccharides for this purpose.

OPS immuno-modulators of the present invention can be obtained from Brucella abortus and other cross reactive bacteria. By way of example, such immuno-modulators can be obtained from the group of bacteria consisting of *Brucella abortus, Brucella suis, Brucella melitensis, Brucella neotomae, Francisella tularensis, Vibrio cholerae, Pseudomonas maltophila* 555, *Escherichia coil* O:157, H:7, *Escherichia coli hermanii, Yersinia enterocolitica* O:9, *Salmonella landau*, and *Salmonella godesberg*.

Similarly, Poly B immuno-modulators for the present invention can be isolated from the group consisting of *Brucella abortus, Brucella suis, Brucella melitensis*, and *Agrobacterium tumefaciens.*

It has previously been shown that bacterial OPS can be synthesized. It is therefore an extension of the present invention to provide synthetic carbohydrates which can replace bacterial OPS as immuno-modulators.

Some strains of Brucella produce both the OPS and the 1,2 beta glucose polymer (Poly B). As both were shown to enhance mouse white blood cell activity, there is the logical extension of the present invention that combinations of polysaccharides may have synergistic immuno-modulating effects.

In a previous study (Cherwonogrodzky et al, 1995), it was found that the OPS could be linked to a carrier (e.g. Lipid A when it formed smooth-lipopolysaccharide, or sLPS) or used within a delivery system (e.g. liposomes). Bacterial or synthetic polysaccharides are also likely to have immuno-modulating effects when used in this manner. Accordingly, in another embodiment, the present invention provides the use of bacterial or synthetic polysaccharides alone, in combination, linked to carriers or in delivery systems (such as liposomes or microspheres) to enhance general immunity (e.g. against bacteria, viruses, fungi, yeasts, parasites and cellular abnormalities).

CONCLUSIONS

As soluble bacterial polysaccharides were shown to be immuno-modulators (i.e. compounds which enhanced phagocytic activity of macrophages to foreign agents), this contradicts the current scientific view that only insoluble carbohydrates have any such effect. Although the inventors do not limit which bacterial polysaccharides may be effective, they did observe that polysaccharides consisting of unusual sugars, unusual conformations or unusual linkages, which were unlikely to be readily metabolized, did enhance the host's cellular activity. They suggest that when the several thousands of bacterial polysaccharides are screened for immuno-modulating effects, that these characteristics be first considered.

When Brucella OPS was used as a vaccine to protect different animal species from brucellosis there appeared to be a wide variation in the dose required for protection: 0.01–0.1 mg for a 25g mouse; 0.1 mg for a 25 kg pig; and, 3 mg for a 200 g guinea pig. If humans have immune systems resembling those of swine rather than rodents, then the effects of the new immuno-modulators of the present invention are likely to be highly effective, long lasting, effective in low dosages, and to not have any ill effects.

The present invention also provides for pharmaceutical compositions containing the synthetic and non-synthetic bacterial polysaccharides. Further, the polysaccharides of the present invention can be administered intramuscularly, subcutaneously, intraperitoneally, orally, or by the respiratory route. The polysaccharides can be given before, during, or after vaccination or infection to enhance immunity.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A method of treating a mammal against an infection caused by a first bacterial species, said method comprising administering intravenously a vaccine comprising a naturally soluble polysaccharide which contains a circular 1,2 β linked glucose, and has been isolated from a second bacterial species to enhance phagocytic activities of macrophages in said mammal, wherein said first bacterial species is from another species than said second bacterial species, wherein said first bacterial species is selected from the group consisting of Brucella and *Haemophilus pleurnpneumoniae.*

2. The method of treating a mammal against an infection caused by a first bacterial species, said method comprising administering an immunomodulator comprising a non-phosphorylated naturally soluble polysaccharide isolated from a second bacterial species to enhance phagocytic activities of macrophages in said mammal, wherein said first bacterial species is from another species than said second bacterial species, wherein said polysaccharide is selected from the group consisting of an outer-polysaccharide, a Polysaccharide B and a polysaccharide cross-reactive therewith, said polysaccharide containing a 1,2 β linked glucose.

3. The method of treating a mammal against an infection caused by a first bacterial species, said method comprising administering an immunomodulator comprising a non-phosphorylated naturally soluble polysaccharide isolated from a second bacterial species to enhance phagocytic activities of macrophages in said mammal, wherein said first bacterial species is from another species than said second bacterial species , wherein said outer-polysaccharide comprises of a polymer of 4-formamido-4,6-dideoxy-D-mannose sugar.

4. The method of treating a mammal against an infection caused by a first bacterial species, said method comprising administering an immunomodulator comprising a non-phosphorylated naturally soluble polysaccharide isolated from a second bacterial species to enhance phagocytic activities of macrophages in said mammal, wherein said first bacterial species is from another species than said second bacterial species, wherein said Polysaccharide B comprises of a polymer of circular 1,2 β linked glucose.

5. The method of treating a mammal against an infection caused by a first bacterial species, said method comprising administering an immunomodulator comprising a non-phosphorylated naturally soluble polysaccharide which contains a circular 1,2 β linked glucose, and has been isolated from a second bacterial species to enhance phagocytic activities of macrophages in said mammal, wherein said first bacterial species is from another species than said second bacterial species, wherein said outer-polysaccharide is extracted from said second bacterial species selected from the group consisting of *Brucella abortus, Brucella suis, Brucella melitensis, Brucella neotomae, Yersinia enterocolitica* O:9 *Francisella tularensis, Vibrio cholerae, Pseudomonas maltophilia* 555, *Escherichia coli* O:15-H:7, *Escherichia hermanii, Salmonella landau, Salmonella gosdesberg* and a cross reactant thereof.

6. The method of treating a mammal against an infection caused by a first bacterial species, said method comprising administering an immunomodulator comprising a non-phosphorylated naturally soluble polysaccharide which contains a circular 1,2 β linked glucose, and has been isolated from a second bacterial species to enhance phagocytic activities of macrophages in said mammal, wherein said first bacterial species is from another species than said second bacterial species, wherein said Polysaccharide B is extracted from said second bacterial species selected from the group consisting of *Brucella abortus, Brucella melitensis* and *Agrobacterium tumefaciens.*

7. The method of treating a mammal against an infection caused by a first bacterial species, said method comprising administering an immunomodulator comprising a non-phosphorylated naturally soluble polysaccharide which contains a circular 1,2 β linked glucose, and has been isolated from a second bacterial species to enhance phagocytic activities of macrophages in said mammal, wherein said first bacterial species is from another species than said second bacterial species, wherein said first bacterial species is selected from the group consisting of Brucella and *Haemophilus pleurnpneumoniae.*

8. A method of treating a mammal against an infection caused by a first bacterial species, said method comprising administering intravenously a vaccine comprising a naturally soluble polysaccharide isolated from a second bacterial species to enhance phagocytic activities of macrophages in said mammal, wherein said first bacterial species is from another species than said second bacterial species, wherein said polysaccharide is selected from the group consisting of an outer-polysaccharide, a Polysaccharide B and a polysaccharide cross-reactive therewith, said polysaccharide containing a circular 1,2 β linked glucose.

9. The method of claim 8, wherein said outer-polysaccharide comprises of a polymer of 4-formamido-4,6-dideoxy-D-mannose sugar.

10. The method of claim 8, wherein said Polysaccharide B comprises of a polymer of 1,2 β linked glucose.

11. A method of claim 8, wherein said outer-polysaccharide is extracted from said second bacterial species selected from the group consisting of *Brucella abortus, Brucella suis, Brucella melitensis, Brucella neotomae, Yersinia enterocolitica* O:9 *Francisella tularensis, Vibrio cholerae, Pseudomonas maltophilia* 555, *Escherichia coli* O:15-H7*, Escherichia hermanii, Salmonella landau, Salmonella gosdesberg* and a cross reactant thereof.

12. A method of claim 8, wherein said Polysaccharide B is extracted from said second bacterial species selected from the group consisting of *Brucella abortus, Brucella melitensis* and *Agrobacterium tumefaciens.*

13. A method of treating a mammal against an infection caused by a first bacterial species, said method comprising administering an immunomodulator comprising a non-phosphorylated polysaccharide isolated from a second bacterial species to enhance phagocytic activities of macrophages in said mammal, wherein said first bacterial species is from another species than said second bacterial species, and said polysaccharide is characterized by being soluble in water.

14. The method of claim 13, wherein said polysaccharide is selected from the group consisting of an outer-polysaccharide, a Polysaccharide B and a polysaccharide cross-reactive therewith.

15. The method of claim 13, wherein said outer-polysaccharide comprises of a polymer of 4-formamido-4, 6-dideoxy-D-mannose sugar.

16. The method of claim 13, wherein said Polysaccharide B comprises of a polymer of circular 1,2 β linked glucose.

17. The method of claim 13, wherein said outer-polysaccharide is extracted from said second bacterial species selected from the group consisting of *Brucella abortus, Brucella suis, Brucella melitensis, Brucella neotomae, Yersinia enterocolitica* O:9 *Francisella tularensis, Vibrio cholerae, Pseudomonas maltophilia* 555, *Escherichia coli* O:15-H: 7*, Escherichia hermannii, Salmonella landau, Salmonella godesberg* and a cross reactant thereof.

18. The method of claim 13, wherein said Polysaccharide B is extracted from said second bacterial species selected from the group consisting of *Brucella abortus, Brucella melitensis* and *Agrobacterium tumefaciens.*

19. The method of claim 13, wherein said first bacterial species is selected from the group consisting of Brucella and *Haemophilus pleuropneumoniae.*

20. A method of treating a mammal against an infection caused by a first bacterial species, said method comprising administering intravenously a vaccine comprising a polysaccharide which contains a circular 1,2 β linked glucose, and has been isolated from a second bacterial species to enhance phagocytic activities of macrophages in said mammal, wherein said first bacterial species is from another species than said second bacterial species, and said polysaccharide is characterized by being soluble in water.

21. A method of claim 20, wherein said first bacterial species is selected from the group consisting of Brucella and *Haemophilus pleuropneumoniae.*

22. A method of claim 20, wherein said polysaccharide is selected from the group consisting of an outer-polysaccharide, a Polysaccharide B and a polysaccharide cross-reactive therewith.

23. The method of claim 22, wherein said outer-polysaccharide comprises of a polymer of 4-formamido-4, 6-dideoxy-D-mannose sugar.

24. The method of claim 22, wherein said Polysaccharide B comprises of a polymer of 1,2 β linked glucose.

25. A method of claim 22, wherein said outer-polysaccharide is extracted from said second bacterial species selected from the group consisting of *Brucella abortus, Brucella suis, Brucella melitensis, Brucella neotomae, Yersinia enterocolitica* O:9 *Francisella tularensis, Vibrio cholerae, Pseudomonas maltophilia* 555, *Escherichia coli* O:15-H:7*, Escherichia hermannii, Salmonella landau, Salmonella godesberg* and a cross reactant thereof.

26. A method of claim 22, wherein said Polysaccharide B is extracted from said second bacterial species selected from the group consisting of *Brucella abortus, Brucella melitensis* and *Agrobacterium tumefaciens.*

* * * * *